United States Patent [19]

Okabe et al.

[11] Patent Number: 5,620,580

[45] Date of Patent: Apr. 15, 1997

[54] IONTOPHORESIS DEVICE

[75] Inventors: Keiichiro Okabe; Toyoji Hibi, both of Tokyo, Japan

[73] Assignee: Hisamitsu Pharmaceutical Co., Inc., Tosu, Japan

[21] Appl. No.: 265,710

[22] Filed: Jun. 23, 1994

[30] Foreign Application Priority Data

Jun. 23, 1993 [JP] Japan .................................. 5-174645
Jun. 30, 1993 [JP] Japan .................................. 5-183399

[51] Int. Cl.⁶ .................................................. A61N 1/30
[52] U.S. Cl. ........................ 204/550; 204/402; 204/403; 204/412; 204/231; 604/20
[58] Field of Search ............................ 604/20; 128/635, 128/640; 607/115, 149, 152, 153; 429/58, 59; 204/402, 403, 411, 412, 299 R, 182.3, 231, 550

[56] References Cited

U.S. PATENT DOCUMENTS

| | | | |
|---|---|---|---|
| 4,731,049 | 3/1988 | Parsi | 604/20 |
| 4,846,950 | 7/1989 | Yao et al. | 204/228 |
| 5,057,072 | 10/1991 | Phipps | 604/20 |
| 5,298,017 | 3/1994 | Theeuwes et al. | 604/20 |
| 5,320,597 | 6/1994 | Sage et al. | 604/20 |

FOREIGN PATENT DOCUMENTS

| | | |
|---|---|---|
| 0556112A1 | 8/1983 | European Pat. Off. . |
| 0483883A1 | 5/1992 | European Pat. Off. . |
| 09302 | 6/1991 | WIPO .................... 204/403 |
| WO9115259 | 10/1991 | WIPO . |

*Primary Examiner*—Kathryn Gorgos
*Assistant Examiner*—Alex Noguerola
*Attorney, Agent, or Firm*—Christie, Parker & Hale, LLP

[57] ABSTRACT

To avoid a reduction of the conductivity in iontophoresis due to the electrical decomposition and the changes in chemical properties of the electrodes themselves, covering by an electrical insulator, and to prevent a drop in the transport rate due to ions freed from the electrode. Provision is made of an electrode structure provided integrally with a reversible electrode and an auxiliary electrode for regeneration of the same and a regeneration current conducting means for conducting a current for regeneration of the reversible electrode when the therapeutic current is off, or the invention is comprised of a reversible electrode and an ion exchange membrane difficult for ions freed from that electrode to penetrate.

13 Claims, 10 Drawing Sheets

930421 Ag-AgCl/Ag
ADIS 4030 2.0v const.

□ NO.1 Im   ◇ NO.2 Im   × NO.4 Im

930420 Ag-AgCl/Ag
DC 2.0v const.

□ NO.1   ◇ NO.2   + NO.3

IONTOPHORESIS DEVICE

BACKGROUND OF THE INVENTION

1. Field of the Invention

The present invention relates to an iontophoresis device and more precisely relates to an iontophoresis electrode structure.

2. Description of the Related Art

The electrodes which are used for iontophoresis for electrically administering aqueous and ionic drugs through the skin are copresent with the solutions containing the drugs and further are mainly supplied continuously or intermittently with therapeutic current of a one-directional polarity.

Electrodes placed under the above-mentioned conditions unavoidably suffer from reduction of their conductivity due to the electrical decomposition and the changes in chemical properties of the electrodes themselves, covering by an electrical insulator, etc.

On the other hand, in the related conventional technology, such as an iontophoresis electrode structure, various types of structures have been proposed, including ones using a so-called reversible (nonpolarized) electrode.

However, when a reversible electrode is used for iontophoresis, the various types of ions freed from the electrode at the time of conductance cause a remarkable drop in the rate of transport of the ionic drug. Therefore, the object of the present invention is to provide a novel electrode structure making it possible to avoid the reduction of conductivity of the electrodes when the electrodes are used in practice, and to obtain efficient iontophoresis preventing as much as possible the drop in the transport rate.

SUMMARY OF THE INVENTION

To attain the above-mentioned objects of the present invention, an iontophoresis device having the following technical structures, is provided.

Namely, the iontophoresis device of the present invention comprises; at least an electrode to which a predetermined level of voltage, for example, predetermined pulses, is applied, a drug holding means which carries ionic drugs therein and is arranged opposite to the electrode, the means being constructed so as to make contact with a portion to which a necessary therapy is required; and a voltage applying control means for applying to the electrode a voltage having a predetermined voltage level at a predetermined timing, wherein the electrode comprises a reversible electrode so that a charge of ions released from the reversible electrode is supplied to the drug held inside the drug holding means through a conductive solution.

More specifically, as a first aspect of the iontophoresis device of the present invention, the iontophoresis device is further characterized in that the reversible electrode is additionally provided with an. auxiliary electrode, and as a second aspect of the iontophoresis device of the present invention, the iontophoresis device is further characterized in that an ion exchange film is provided between the reversible electrode and the drug holding means.

DETAILED DESCRIPTION OF THE PREFERRED EMBODIMENT

The iontophoresis device of the present invention will be explained in detail hereafter with reference to the attached drawings.

Figure 1:
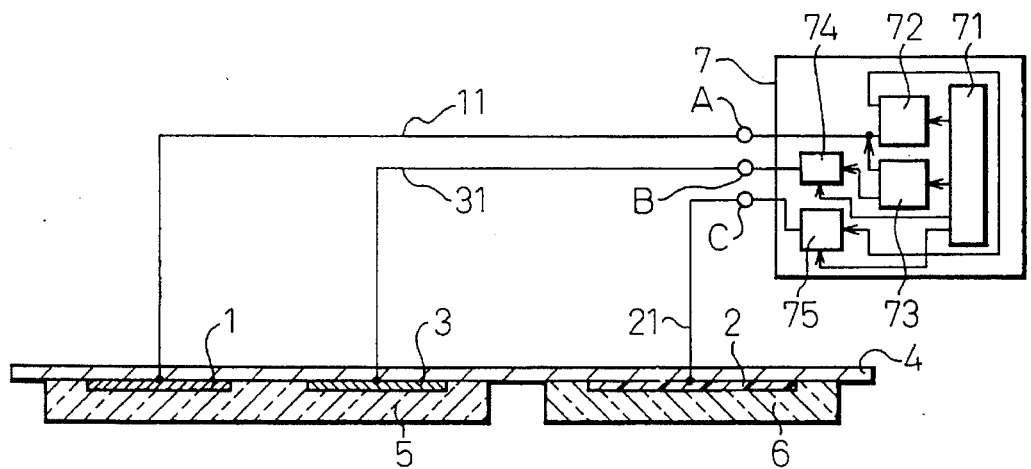
FIG. 1 is a partial sectional view showing a first embodiment of the present invention.

FIG. 1 shows a block-diagram indicating one embodiment of a basic technical construction of the iontophoresis device in the present invention. As explained above, the iontophoresis device of the present invention comprises; at least an electrode 1 or 2 to which a predetermined level of voltage, for example, predetermined pulses, is applied; a drug holding means 5 which carries ionic drugs therein and is arranged opposite to the electrode 1 or 2, the means being: constructed so as to make contact with a portion to which a necessary therapy is required; and a voltage applying control means 7 for applying to the electrode 1 or 2 a voltage having a predetermined voltage level at a predetermined timing. The electrode 1 or 2 comprises a reversible electrode so that a charge of ions released from the reversible electrode is supplied to the drug held inside the drug holding means 5 through a conductive solution.

Further in a first aspect of the present invention, the iontophoresis device 1 or 2 of the present invention, is additionally provided with an auxiliary electrode 3, and in a second aspect of the present invention, the iontophoresis device is further characterized in that an ion exchange film 13 (not shown) is provided between the reversible electrode 1 or 2 and the drug holding means 5.

The technical construction of the first aspect of the iontophoresis device of the present invention will be explained next.

As explained above, the first aspect of the iontophoresis device defined by the present invention, has the above-mentioned basic technical construction as well as the additional technical feature in that the reversible electrode 1 or 2 is accompanied by the auxiliary electrode 3, Note that the first aspect of the present invention provides an electrode structure provided integrally with a reversible electrode and an auxiliary electrode for regeneration of the same and a regeneration current conducting means for conducting a current for regeneration of the reversible electrode when the therapeutic current is off so as thereby to prevent an electrode reaction of the main electrode and counter electrode impairing the conductivity or to restore the conductivity along with regeneration of the electrodes.

EXAMPLE 1

Therefore, one embodiment of the first aspect of the iontophoresis device concerning the present invention will be explained in Example 1.

In FIG. 1, 1 is an electrode for the main electrode which is comprised of a metal material such as Ag. The material is selected in accordance with the polarity of the main electrode.

Reference numeral 2 is an electrode for a counter electrode which is comprised of AgCl, Ag, etc. The material of the electrode 2 for the counter electrode is similar to the electrode 1 for the main electrode. A member with reversibility is selectively used for the electrode 1 for the main electrode and the electrode 2 for the counter electrode. "Reversibility" means that all or part of the electrode can be regenerated to the original material or the original conductivity. As a typical material, silver Ag is shown, but the invention is not limited to this.

Further, the polarities of the main electrode and the counter electrode are determined by the ionic polarities of the drug being administered and may be a positive polarity or a negative polarity.

Reference numeral 3 is an auxiliary electrode for regeneration use and is comprised of a conductive material such as aluminum. Reference numeral 4 is a backing member and is a sheet-like member having an electrical insulation ability.

The electrodes 1 to 3 are attached to the surface of the backing member 4 by printing, adhesion by an adhesive, etc.

Reference numeral 5 is a drug holding means which is comprised of a porous member in which a drug and solution are impregnated.

As an example of a porous member, a water-absorbing and water-permeable film-like member is shown.

As a water-absorbing and water-permeable film-like member, illustration may be made of a laminar shaped membrane filter (Biodyne A (trademark)), paper, nonwoven fabric, porous film, or other moisture-permeating fiber layer, starch (oblate) formed by an aqueous polymer holding, adhered with, or containing a predetermined drug, a PVP film or other water-absorbing (water soluble) film, usually used to form a thin film. Further, the degree of the water solubility may be suitably adjusted in accordance with the purpose of use.

Reference numeral 6 is an interface forming means, which is comprised of a porous member as above, a gel substrate, etc. impregnated with a conductive solution.

Reference numeral 7 is a power supply unit, whose internal structure will be explained below. Reference numeral 71 is a signal processing unit, which houses predetermined algorithmns and outputs control signals based on those algorithmns. The signal processing unit 71 is comprised by a gate array, a microcomputer, etc. Reference numeral 72 is a therapeutic current pulse output means, which outputs pulses and outputs depolarized pulses. The frequency and duty are not particularly limited. Reference numeral 73 is a regeneration electrical output means, which outputs a direct current, pulses, etc. The therapeutic current pulse output means 72 and the regeneration electrical output means 73 are controlled in accordance with need by the signal processing unit 71. Reference numerals 74 and 75 are switching means, which are comprised of analog switches, relays, transistors, FET's, etc. The switching means 74 and 75 perform an ON/OFF operation by control signals output by the signal processing means 71. One end of the output of the therapeutic current pulse output means 72 is connected to the output terminal (A), while the other end is connected to one end of the switching means 75. The other end of the switching means 75 is connected to the output terminal (C). One end of the regeneration electrical output means 73 is connected to the output terminal (A), while the other end is connected to one end of the switching means 74. The other end of the switching means 74 is connected to the output terminal (B). The depolarized pulse output means has the function of connecting the output terminals when the output pulse is off. For more details, see the description in the Japanese Unexamined Patent Publication (Kokai) No. 60-156475. Reference numerals 11, 21, and 31 are lead wires, which electrically connect the output terminals (A) to (C) of the power supply unit 7 and the electrodes 1 to 3.

Next, the operation of the construction shown in FIG. 1 will be explained in detail with reference to FIGS. 2(A) and (B) and FIGS. 3(A) to (C). The drug holding means 5 and interface forming means 6 of FIG. 1 are made to abut adjust the locations of percutaneous administration of the drug and the power supply unit 7 operated. The signal processing means 71 turns on the switching means 75 and turns off the switching means 74. The therapeutic current pulse output means outputs the therapeutic current pulse and outputs the pulse shown in FIG. 2(A) to the output terminal (A) and the output terminal (C).

The output terminal (B) is in a state electrically shut off from other output terminals since the switching means 74 is off. The output terminal (A) is connected to the electrode i of the main electrode, while the output terminal (C) is connected to the electrode 2 of the counter electrode. At the same time the pulse rises, a closed electrical circuit is formed among the drug holding forming means 5, the human body, and the interface forming means 6 and the therapeutic current flows.

Figure 2A:
FIGS. 2(A), 2(B) and FIGS. 3(A), 3(B) and 3(C) are views for explaining the operation of the embodiment shown in FIG. 1.

When the pulse shown in FIG. 2(A) falls, the signal processing means 71 turns off the switching means 75 and turns on the switching means 74. The power supply unit 7 outputs a regeneration pulse shown in FIG. 2(B) between the output terminal (A) and the output terminal (B). At this time, the polarity of the pulse of the output terminal (A) is opposite to the polarity at the time of previous output of the therapeutic current. For example, if the output terminal (A) had a positive polarity at the time of output of the therapeutic current, the output terminal (A) has a negative polarity and the output terminal (B) has a positive electrode at the time of output of the regeneration pulse. The regeneration pulse output to the output terminal (B) and the output terminal (A) creates a closed electrical circuit among the regeneration electrode 3, the drug holding means 5, and the electrode and 1 of the main electrode, applies a reverse direction voltage so as to prevent the electrode reaction of the electrode 1 of the main electrode, and thereby regenerates the conductivity.

Further, the output terminal (C) is set to become electrically shut off from the other output terminals since the switching means 75 is off. Further, when the electrical conductivity of the drug holding means 5 is high, the power supply unit 7 sometimes connects the resistor on the closed electrical circuit formed between the output terminal (B) and the output terminal (A) so as to prevent surcharge current from generating in this circuit when the operation for regenerating the electrode is carried out.

Further, the power supply unit 7 is not limited so long as it is provided with a battery or other power source and a main pulse output means, depolarized pulse output means, direct current output means, and a device for controlling these output devices. Further, since the output current and voltage are relatively small, it is easy to make the key portions of the power supply unit 7 on a single chip.

The above embodiment is one in which a regeneration pulse is output each time a therapeutic current pulse is output. Next, however, an explanation will be made of a different operation. The construction is the same as that in FIG. 1, so the explanation of the construction will be omitted.

Figure 3A:
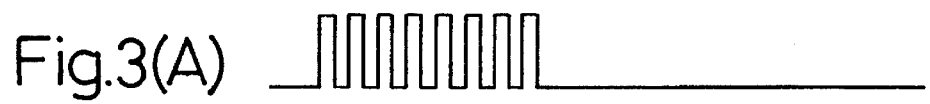
Figure 3B:
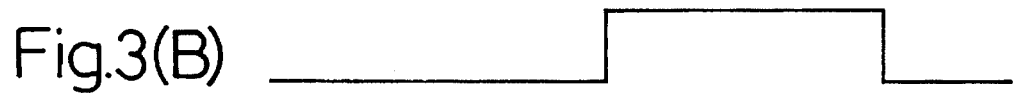
Figure 3C:

In FIG. 1, the power supply unit 7 outputs the therapeutic current pulse shown in FIGS. 3(A) to (C) to the output terminal (A) and the output terminal (C) for exactly a predetermined period of time. At this time, the output terminal (B) is in a state electrically shut off from the other outputs.

Next, the regeneration direct current shown in FIG. 3(B) is output across the output terminal (B) and the output terminal (A) for a predetermined time. At this time, the output terminal (C) is in an electrically shut off state. The "direct current" spoken of here includes a pulse with a long pulse width.

Figure 2B:

The regeneration pulse output across the output terminal (B) and the output terminal (A) may be, in addition to the direct current shown in FIG. 2(B), a group of successive pulses as shown in FIG. 3(C) or a depolarized pulse.

The time the therapeutic current pulse is held may be several hours, for example, three hours or preferably six hours or so, but is not particularly limited. Further, the time the regeneration current output is sustained may be, for example, one hour, preferably three hours, but is not particularly limited.

EXAMPLE 2

Next, an explanation will be made of another embodiment of the first aspect of the iontophoresis device of the present invention and will be explained in Example 2 with reference to FIG. 4.

Reference numeral 1 is an electrode for the main electrode, and 3 is an auxiliary electrode. The electrode 1 for the main electrode and the auxiliary electrode 3 are both formed of conductive members having holes.

Reference numeral 32 is a support member, which is formed by a nonconductive porous member such as a nonwoven fabric. The electrode 1 for the main electrode and the auxiliary electrode 3 are printed on the front and rear of the support member 32 or are affixed to it by mechanical or chemical bonding.

Reference numeral 5 is drug holding means which has the above-mentioned structure.

Reference numeral 33 is a connecting member which is formed by a conductive member including the same material as the drug holding means 5. The lead wire 11 for connecting the electrode 1 for the main electrode with the power supply unit 7 shown in FIG. 1 and the lead wire 31 for connecting the auxiliary electrode 3 and the power supply unit 7 are the same as those shown in FIG. 1.

Figure 4:
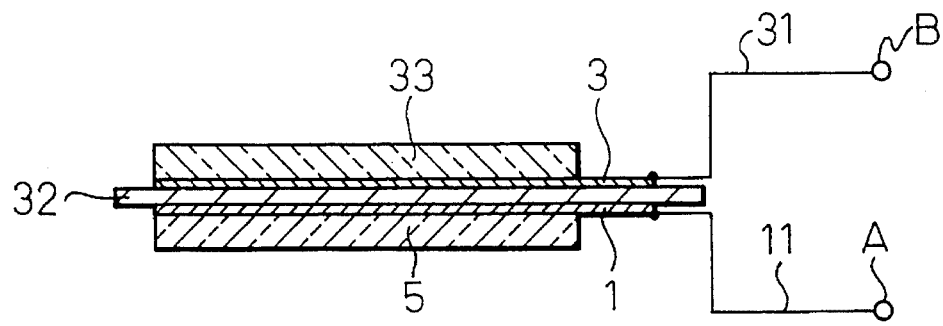
FIG. 4 and FIG. 5 are views showing a second embodiment of the present invention.

FIG. 4 shows the construction with the electrode for the main electrode and the electrode for the counter electrode separated. The counter electrode side is shown by the same reference numerals and illustration is omitted.

Further, the above separation is not particularly necessary. The electrodes may be formed integrally as well as shown in FIG. 1. Further, the holes made in the electrode for the main electrode and the auxiliary electrode are not particularly necessary. The point is that the drug holding means 5 and the connecting member 33 be of a structure forming an electrically conductive state through the support member 32.

Next, the operation will be explained.

The electrical output of the power supply unit 7 is the same as that explained with reference to the operation of FIG. 1. The support member 32 is porous, so the drug holding means 5 and the connecting member 33 are electrically conductive in state through the solution.

Accordingly, after a pulse for the therapeutic current is output across the output terminal (A) and the output terminal (B) in the same way as in FIG. 1, when a regeneration pulse is output across the output terminal (A) and the output terminal (B), a closed electrical circuit is formed between the electrode 1 for the main electrode and the auxiliary electrode 3 and the operation of regeneration of the electrode 1 for the main electrode is performed.

EXAMPLE 3

Next, another embodiment of the first aspect of the ionophoresis device of the present invention will be explained as Example 3, with reference to FIG. 5.

Figure 5:
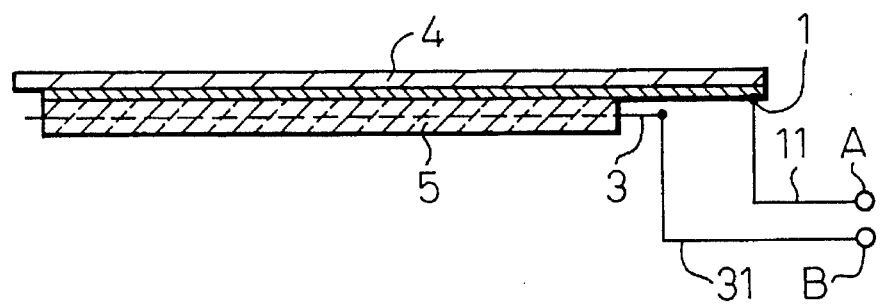

FIG. 5 shows the drug holding means 5 shown in FIG. 1 inside of which has been interposed an auxiliary electrode 3 having a mesh shape or holes. The rest of the construction is the same as in FIG. 1 and the operation is the same as in FIG. 2, so an explanation of these will be omitted. The auxiliary electrode 3 may be a conductor member itself or may be a member comprised of a nonconductive sheet in which is made holes for attachment of the conductor member.

Next, examples of the drugs used in the present, invention will be shown.

Local anesthetic
    Lidocaine hydrochloride
    Tetracaine hydrochloride
    Procaine hydrochloride
    Dibucaine hydrochloride
    Oxybuprocaine hydrochloride
    Bupivacaine hydrochloride
    Mepivacaine hydrochloride Antiallergic agent or Antitussant and expectorant
    Sodium cromoglicate
    Ketotifen fumarate
    Azelastine hydrochloride
    Amlexanox
    Terrenadine
    Emedastine fumarate
    Tranilast
    Codeine phosphate
    Dihydrocodeine phosphate
    Eprazinone hydrochloride
    Tipepidine hibenzate Bronchial dilator
    Theophylline
    Pirbuterol hydrochloride
    Terbutaline sulfate
    Hexoprenaline sulfate
    Salbutamol sulfate Tulobuterol hydrochloride
Procaterol hydrochloride
Mabuterol hydrochloride
Formoterol fumarate
Analgesics
  Morphine hydrochloride
  Hydromorphone hydrochloride
  Buprenorphine hydrochloride
  Bupranolol hydrochloride
  Pentazocine hydrochloride
  Butorphanol tartarate
  Eptazocine hydrobromido
  Nalbuphine hydrochloride
  Pentazosin lactate
  Dichlorophenac sodium
Cardiacs
  Dopamin hydrochloride
  Dobutamine hydrochloride
  Amrinone
Tranquilizers
  Chlorpromazine hydrochloride
  Etizolam
  Amitriptyline hydrochloride
  Clocapramine dihydrochloride
  Haloperidol
  Mosapramine hydrochloride
  Perphenazine
  Phenothiozine
Antibiotics
  Cloxacillin sodium
  Benzylpenicillin potassium
  Ticarcillin sodium
  Ampicillin sodium
  Piperacillin sodium
  Cefoxitin sodium
  Cefodizime sodium
  Cefotaxime sodium
  Cefotetan
  Cefotetany sodium
  Cefoperazone sodium
  Cefsulodin sodium
  Ceftazidime
  Cefmetazole sodium
  Cefpirome sulfate
  Gentamicin suifate
  Sisomicin sulfate
  Dibekacin sulfate
  Netilmicin sulfate
  Amikacin sulfate
  Ribostamycin sulfate
  Lincomycin
  Erythromycin
  Josamycin
  Chloramphenicol
  Tetracycline
Antimelanoma agents
  Mitomycin C
  Etoposide
  Procarbazine hydrochloride
  Tamoxifen citrate
  Fluorouracil
  UFT®
  Tegafur
  Carmofur
  Methotrexate
  Carboquone
  Bleomycin hydrochloride
  Peplomycin sulfate
  Epirubicin hydrochloride
  Pirarubicin hydrochloride
  Neocarzinostatin
  Lentinan
  Picibanil
  Sizofilan
  Cisplatin
  Carboplatin
  Adriamycin
  Vincristine sulfate
Circulatory medicines
  Nicametate titrate
  Alprostadil
  Argatroban
  Citicoline
  Nizofenone fumarate
  D-Mannitol
  Nicorandil
  Diltiazem hydrochloride
  Mecrophenoxate hydrochloride
  Rhislid maleate
  Calcium hopantenate
Gout treatment agents
  Benzbromarone
  Allopurinol
  Colchicine
High lipemia agents
  Simvastatin
  Nicomol
  Pravastatin sodium
Antihistamines
  Diphenhydramine hydrochloride
  Promethazine hydrochloride
  Chlorpheniramine maleate
  Mequitazine
  Clemastine fumarate
Sleep abirriant agents or Antianxiety agents
  Flunitrazepam
  Midazolam
  Secobarbital sodium
  Amobarbital sodium
  Phenytoin sodium
Analgestics or Antiphlogistics
  Ketoprofen
  Flurbiprofen axetil
  Indometacin
  Loxoprofen sodium
  Diclofenac sodium
  Piroxicam
  Tenidap
  Flurbiprofen
  Tenoxicam
Antivertigo agents
  Difenidol hydrochloride
  Thiethylperazine maleate
  Betahistine mesylate
Anti-convulsants
  Scopolamine Buthylbromide
  Atropine sulfate
  Eperisone hydrochloride
  Tizanidine hydrochloride
Arrhythmia agents
  Arotinolol hydrochloride
  Propanolol hydrochloride
  Atenolol
  Quinidine sulfate Indenolol hydrochloride
Bucumolol hydrochloride
Antihypertensive agent
  Clonidine hydrochloride
  Bethanidine sulphate
  Benazepril hydrochloride
  Cilazapril
  Captopril
  Celiprolol hydrochloride
  Tilisolol hydrochloride
  Terazosinn hydrochloride
  Bunazosin hydrochloride
  Carvedilol hydrochloride
Cortical hormones
  Hydrocortisone sodium phosphate
  Dexamethasone palmitate
  Dexamethasone sodium phosphate
  Betamethasone sodium phosphate
  Methylprednisolone succinate
Peptide, Polypeptide and others
  Luteinizing hormone-releasing hormone (LH-RH)
  Enkephalin
  Endorphin
  Interferon
  Insulin
  Calcitonine
  Thyrotropin releasing hormone (TRH)
  Oxytocin
  Lypressin
  Vasopressin
  Glucagon
  Pituitary hormone
  Human growth hormone (HGH)
  Human menopausal gonadotrophin (HMG)
  Human chorionic gonadotrophin (HCG)
  Desmopressin acetate
  Follicile-stimulating hormone
  Growth hormone-releasing factor
  Adrenocorticotropic hormone (ACTH)
  Parathyroid hormone (PTH)
  Secretin
  Angiotensin
  β-Endorphin
  Somatostatin
  Gastrin
  Neurotensin
  Atrial natriuretic peptide (ANP)
  Bradykinin
  Substance P
  Dynorphin
  Thyroid-stimulating hormone (TSH)
  Prolactin
  Interleukin
  Filgrastim
  Glutathione peroxidase
  Superoxide dismutase (SOD)
  Desmopressin
  Somatromedin
  Melanocyte-stimulating hormone (MSH)
  Muramyl dipeptide
  Bombesin
  Vasoactive intestinal polypeptide
  Cholecystokinin-8
  Calcitonin gene relating peptide (CGRP)
  Endothelin
  Nicotine These agents are mixed with various matrix components available in pharmaceutics and can be used in various types of forms such as salve, gel, cream, solution, suspension film and the like.

As explained above, in the first aspect of the iontophoresis device of the present invention, the auxiliary electrode may preferably be arranged integrally with the reversible electrode and further the auxiliary electrode may preferably be controlled by the voltage applying controlling means so that the auxiliary electrode is supplied with predetermined pulses at a timing at which predetermined pulses are not applied to the reversible electrode, Further in the first aspect of the present invention, at least two reversible electrodes are provided in the iontophoresis device and two of the reversible electrodes, selected from among them, preferably form a pair as one group, and in that each one of the reversible electrodes forming the pair, is supplied with the pulses. The pulse phase of the pulses applied to one of the reversible electrodes in the pair, is different from that of the pulses applied to another reversible electrode in the pair.

On the other hand, in the first aspect of the present invention, the auxiliary electrode provided in the iontophoresis device, is arranged at a position close to one of the reversible electrodes forming the pair of groups, and more particularly, the auxiliary electrode may be provided on a plane of the device identical to the plane on which the reversible electrode is provided or may be provided to form a construction in which the auxiliary electrode is stacked with the reversible electrode through a supporting means interposed therebetween.

Next, an explanation will be given of experiments of the first aspect of the iontophoresis device of the present invention about a mode of function and effect thereof.

EXPERIMENT 1

Figure 6:
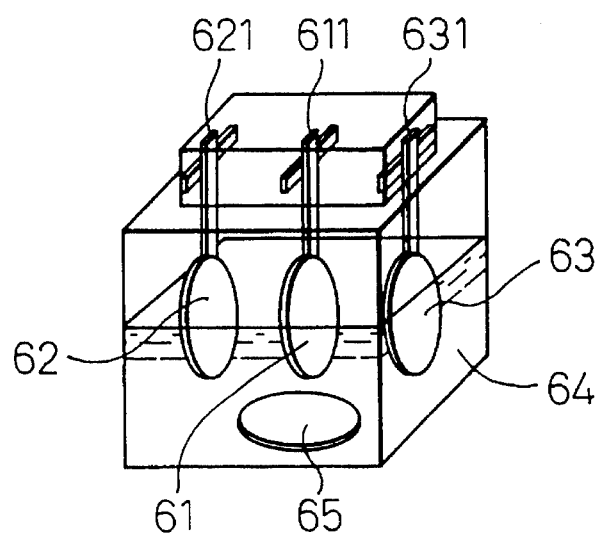
FIG. 6 is a view showing the configuration of a device at the time of performing experiments regarding the embodiment of the present invention.

The experimental apparatus is shown in FIG. 6. Reference numeral 61 is an anode use electrode (main electrode), which is comprised of silver (Ag) foil.

Reference numeral 62 is an anode use electrode (auxiliary electrode) comprised of a carbon printed film electrode.

Reference numeral 63 is a cathode use electrode (counter electrode) which is comprised of an AgCl/Ag foil.

Reference numeral 64 is a physiological saline solution, while 65 is a stirrer.

The distance between electrodes was made 25 mm and the electrical output device for the therapeutic current used was a 2 V, 40 kMz, 30 percent duty depolarized pulse output device. The regeneration use electrical output device used was also a depolarized pulse output device similar to the above. The electrodes 61 to 63 and the electrical output means were connected by conductor terminals 611 to 631.

A current was output for the therapeutic current so that the anode use electrode (main electrode) 61 became positive and the cathode use electrode (counter electrode) became negative. When the current value dropped to about half of the initial value, the conductance was stopped and the weight of the electrodes was measured. (The conductance time was 15 to 20 minutes.) Then, a DC current corresponding to the amount of AgCl produced at the anode electrode (main electrode) 61 (calculated by the Faraday Law shown in equation 1) were output for regeneration so as to make the anode electrode (auxiliary electrode) 62 positive and the anode electrode (main electrode) 61 negative. (The time of output of the electrical output for regeneration was approximately 7.85 mA×9 minutes to 12 minutes.)

Equation 1) $It = F \cdot W/Me$ where,

I: current value (A)

t: time (seconds)

F: Faraday constant $9.65 \times 10^3$ (c/mol)

w: Mass of reaction substance (g)

Me: Chemical equivalents (g/mol)

Figure 7:
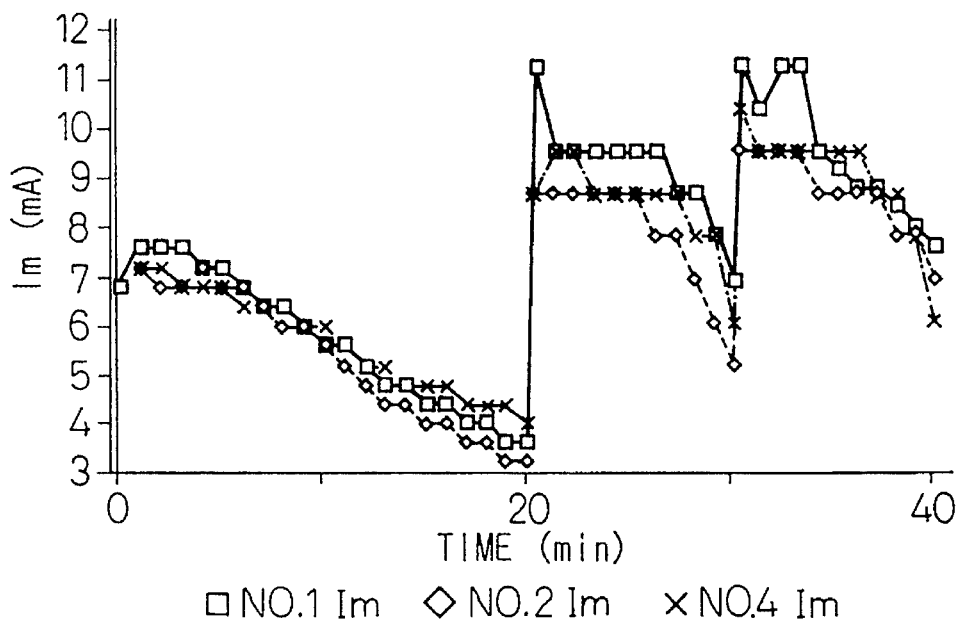
FIG. 7 and FIG. 8 are views showing results of the experiments.

After the anode electrode (main electrode) 61 was regenerated from AgCl to Ag, the above-mentioned electrical current for therapeutic current was applied across the anode electrode (main electrode) 61 and the cathode electrode (counter electrode) 63 once again. These steps were repeated and about three examples were measured. The results are shown in FIG. 7. The graph represented by a symbol □ in FIG. 7, shows a first embodiment of the above-mentioned test resul and the graph shows the relationship between the electrical current for therapeutic current Im and time for the therapeutic treatment.

In FIG. 7, the graph indicates that although the initial current value Im (measured at the time 0) shows 8 mA, the current value Im was reduced to 3.5 mA when 20 minutes (20 min) has passed. Therefore, at this period, the electrical current for therapeutic current Im was once stopped and the regenerating operation as defined by the present invention was carried out (a first regenerating operation). After this regenerating operation was completed, the second electrical current for therapeutic current Im was again supplied.

Further, when 30 minutes (30 min) passed, the electrical current for therapeutic current Im was again stopped and the regenerating operation as defined by the present invention was carried out (a second regenerating operation). After this regenerating operation was completed, the third electrical current for therapeutic current Im was again supplied.

On the other hand, the other graphs represented by symbols ◊ and x, respectively, show the relationships between the electrical current for therapeutic current Im and time for the therapeutic treatment of a second and a third embodiment of the above-mentioned test result, carried out under the same manner as that of the above-mentioned first embodiment, respectively.

As shown in FIG. 7, and in any one of the embodiments, when the first and the second regenerating operation had been carried out, the value of the electrical current has always exceeded the initial current value of 8 mA and it had been increased up to 9 to 10 mA, respectively.

Accordingly, regeneration of the anode electrode (main electrode) was confirmed.

EXPERIMENT 2

Figure 8:
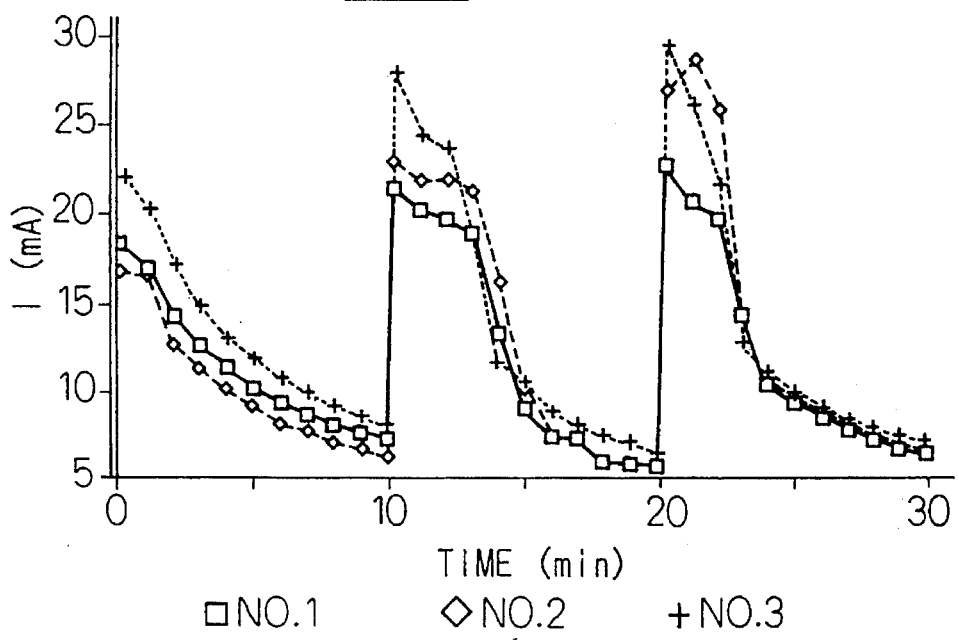

The same type of experiment as in Experiment 1 was performed except that the electrical output of the regeneration electrical output device used in Experiment 1 was made a direct current stabilized to a voltage of 2.0 V. The results are shown in FIG. 8. FIG. 8 enabled confirmation of the regeneration of the anode electrode (main electrode) in the same way as FIG. 7.

As explained above, the present invention has the effects of restoring conductivity by preventing an electrode reaction impairing the conductivity or by regeneration of the electrode and enables stable, effective administration of a drug over a long period.

Next, a second aspect of the iontophoresis device of the present invention will be explained with respect to its technical structure, with reference to the attached figures.

Figure 10:
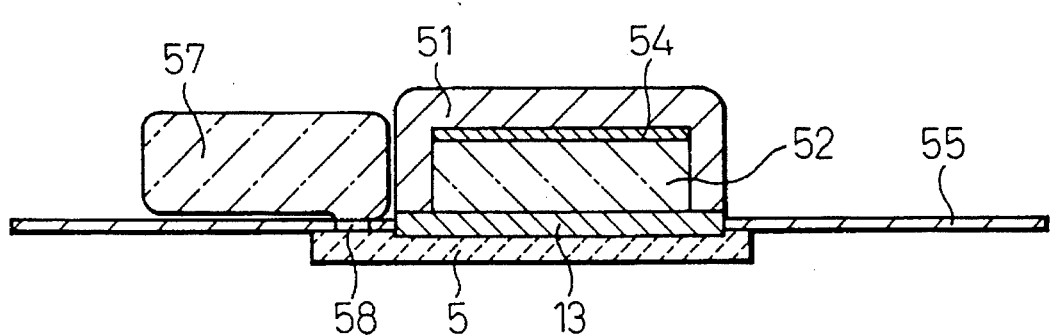
FIG. 10 is a sectional view of a third embodiment of the present invention.
Figure 11:
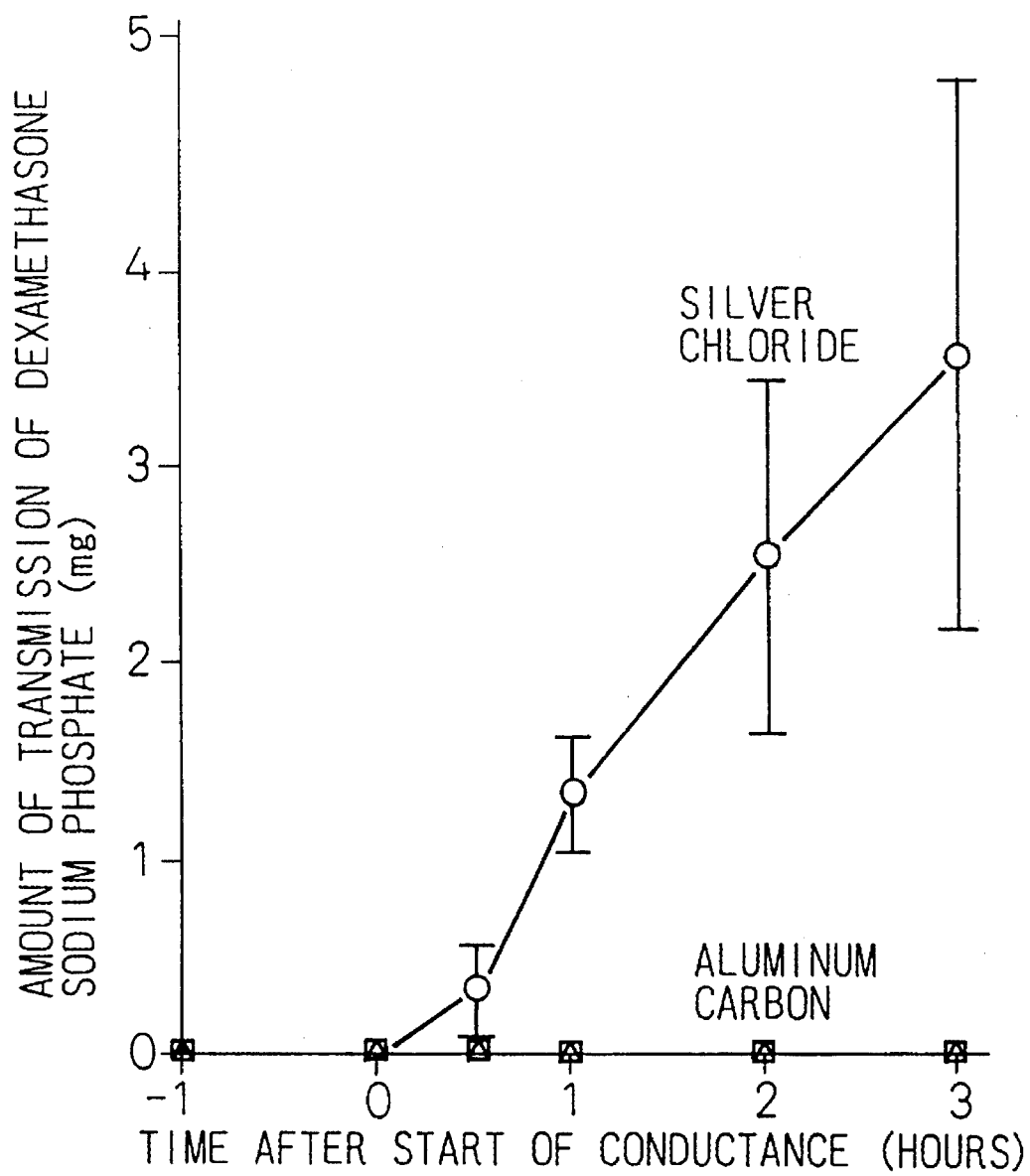
FIG. 11 and FIGS. 12(A) and (B) are views showing the results of Experiment 1.

FIG. 10 is a schematic sectional view of the second aspect of the iontophoresis device of the present invention in which, in the iontophoresis device, an ion exchange film 13 is provided between the reversible electrode 54 and the drug holding means 5. Further in the second aspect of the present invention, the ion exchange film 13, used in the iontophoresis device, has a characteristic in which it is difficult for ions freed from the electrode 54 to penetrate through the film 13. Moreover, in the second aspect of the present invention, conductive solution 52 used in the iontophoresis device is interposed between the ion exchange film 13 and the reversible electrode 54.

In another embodiment of the second aspect of the present invention, the drug holding means 5 is provided with a drug solution supply means 57 connected to the drug holding means 5.

As the reversible (nonpolarized) electrode in the present invention, illustration may be made of a silver (Ag) or silver chloride (AgCl) electrode. Here, when trying to administer an ionic drug using a reversible (nonpolarized electrode) such as one of silver (Ag) or silver chloride (AgCl), the silver ions ($Ag^+$), chlorine ions ($Cl^-$), etc. freed from the electrode at the time of conductance cause a remarkable drop in the transport rate of the drugs, so use is made of an ion exchange membrane which is difficult for these freed ions to pass through.

Figure 9:
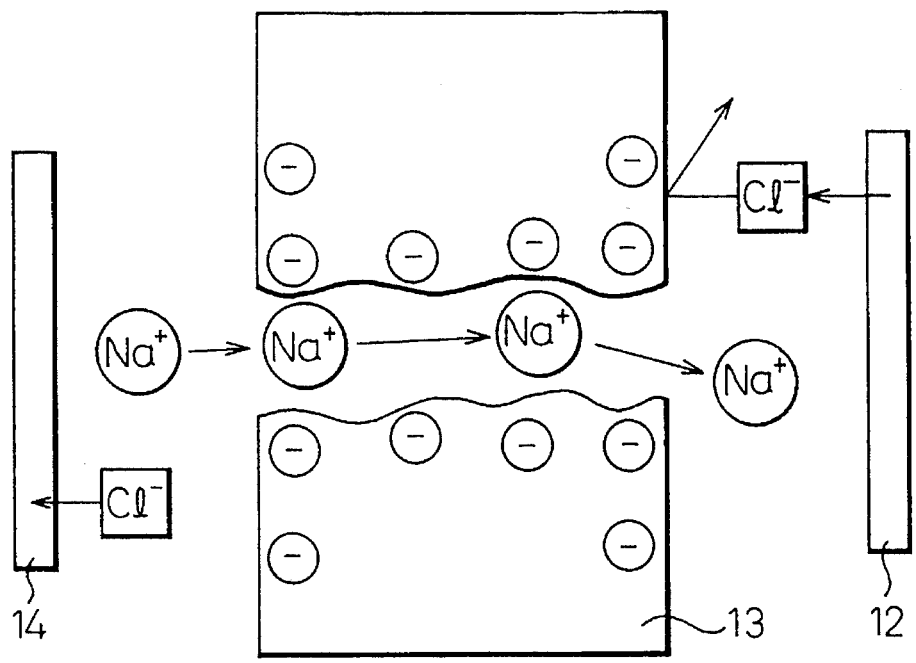
FIG. 9 is a schematic view of ion exchange membrane.

An explanation will now be made of the selective transmission of a positive ion exchange membrane which is used in the second aspect of the present invention, with reference to FIG. 9. Movement of ions through the membrane occurs along with the electrochemical potential, but the positive ion exchange membrane 13 has a negative charge, so the negative ions (chlorine ions) freed from the negative electrode (silver chloride) 12 are much slower in speed or, movement compared with the positive ions due to the electrical repulsion. Reference numeral 14 shows the positive electrode (silver). That is, when the freed ions are negative ions, use is made of a positive ion exchange membrane, while when they are positive ions, use is made of a negative ion exchange membrane. As a preferable ion exchange membrane, mention may be made of the following: Neosepta (registered trademark) CMS (made by Tokuyama Soda Co.) for the positive ion exchange membrane and Neosepta (registered trademark) ACM for the negative ion exchange membrane (made by Tokuyama Soda Co.)

Next, an explanation will now be made of a principle of an operation of an embodiment of the above-mentioned embodiment using FIG. 10. In FIG. 10, 51 is an aqueous solution supply member, which is constructed as an ampoule, container, pouch, etc. which contains an aqueous solution 52 for dissolving the drug at the time of use and forming a conduction path. Reference numeral 13 is an ion exchange membrane for suppressing the flow of various ions freed from the electrode at the time of conductance. Reference numeral 54 is an electrode made of silver (Ag), silver chloride (AgCl), etc. Reference numeral 55 is an adhesive layer. The drug used is deposited on or impregnated in a drug holding member 5, for example, a porous membrane (Biodyne (registered. trademark) A etc.), paper, nonwoven fabric, soluble starch (oblate), sodium polyacrylate, polyvinyl alcohol, or any other water-permeable material. Further, the system of dissolving the drug at the time of use may also be used, i.e., where the drug is stored in a dry state on the drug holding member 5, the drug dissolving liquid is passed from the drug solution supply member 57 having a reserve structure, such as an ampoule, container, pouch, etc. to fine holes 58 to permeate to the drug holding member 5 and dissolve the drug. Further, when the water permeability of the ion exchange membrane 13 is sufficient for the supply of water to the drug holding member 5, the drug solution supply member 57 and the fine holes 58 may be omitted.

Before showing experiments conducted regarding the embodiment of the present invention, based on the results of comparative experiments on reversible (nonpolarized) electrodes where chlorine ions are released during conductance and polarized electrodes where ions are not released, the present applicant showed the superiority of a reversible (nonpolarized) electrode to a polarized electrode in the previously proposed pulse depolarization type iontophoresis (Japanese Examined Patent Publication (Kokoku) No. 2-45461) and confirmed the efficacy, importance, and necessity of the iontophoresis electrode structure of the present invention, which enables the drug transport efficiency to be raised in case a silver chloride electrode is used which discharges chlorine ions along with conductance.

EXPERIMENT 1

Next, a relationship between the ion exchange membrane and a material used for the electrode will be explained, hereafter.

Figure 12A:
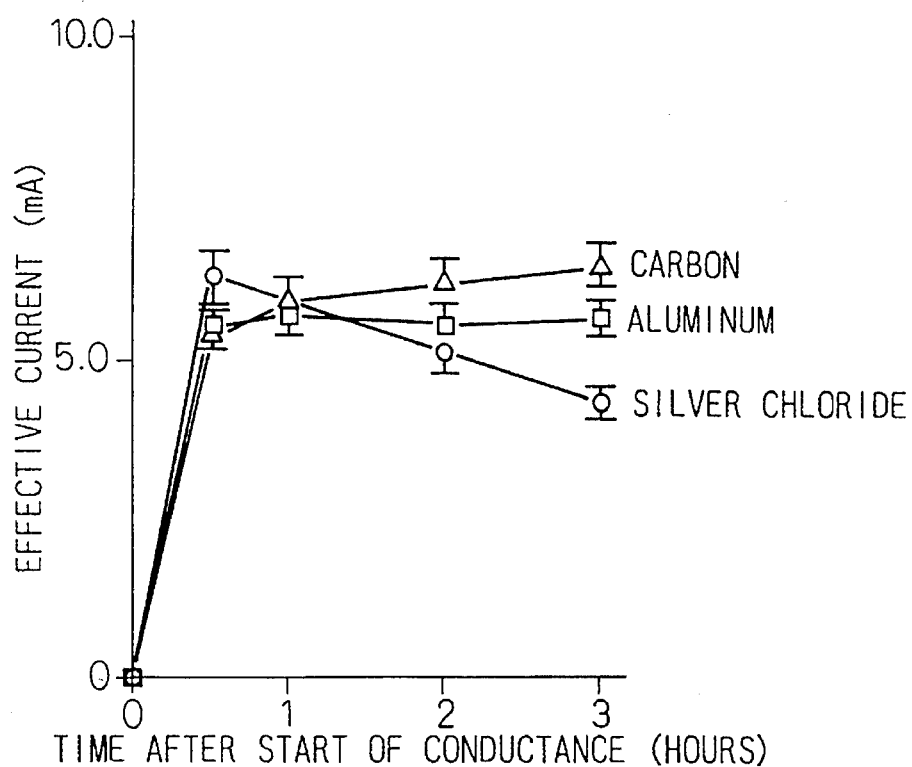
Figure 12B:
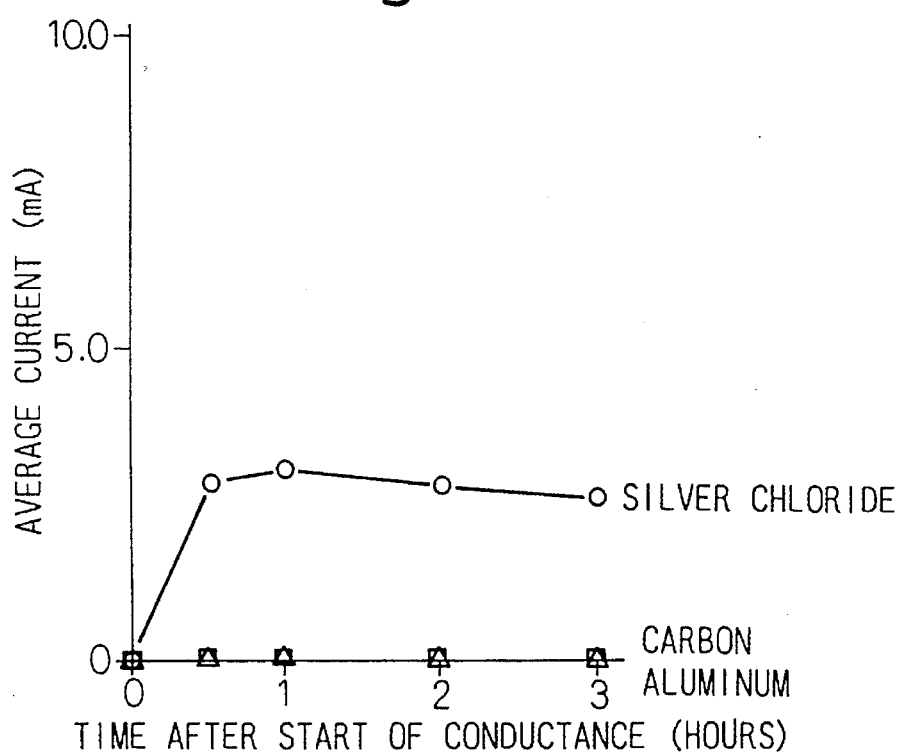
Figure 13A:
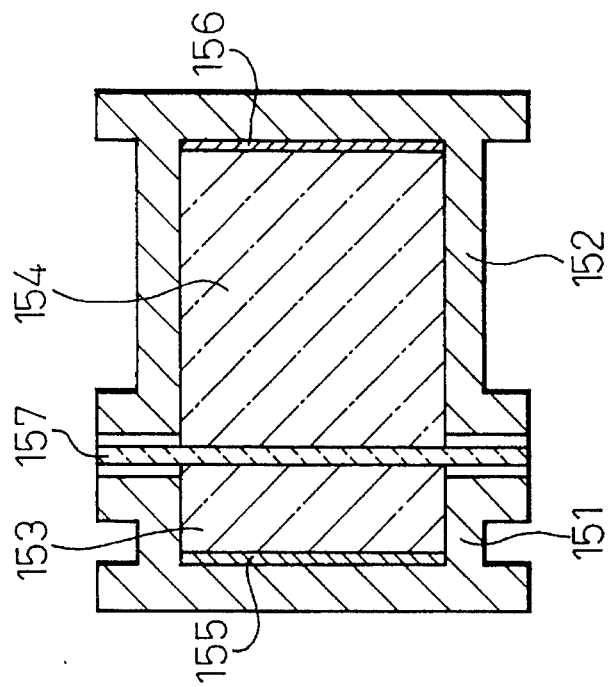
FIGS. 13(A) and (B) are a sectional view of an experimental apparatus in the experiment on the embodiment of the present invention.
Figure 13B:
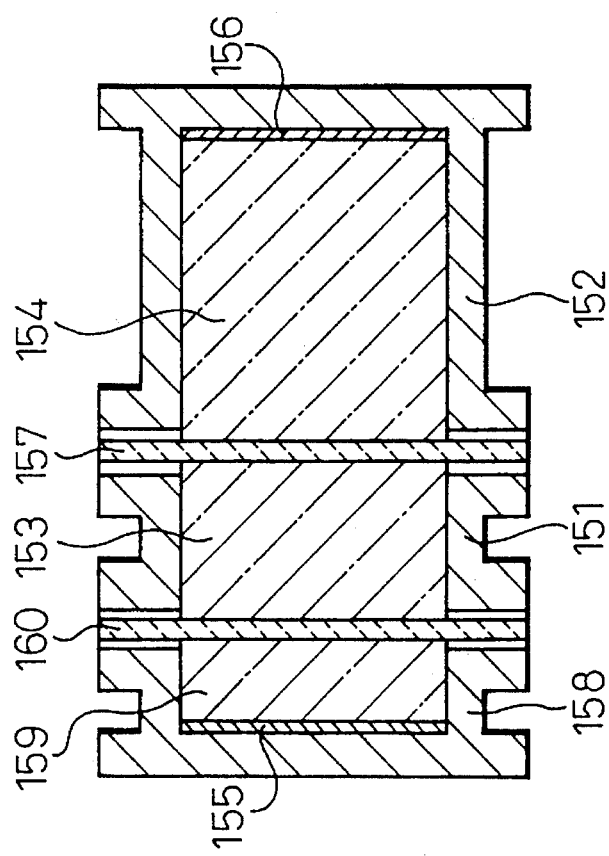

The abdominal skin 157 of seven week old hairless rats was excised and was attached with the corneal layer facing the drug container side to the two-container type horizontal diffusion cell (drug transmission area: 2.54 $cm^2$) of the basic structure shown in FIG. 13(B). The drug container 151 and drug receiving container 152 were filled with 1.5 percent aqueous dexamethasone sodium phosphate solution 153 and phosphate buffered saline solution (PBS) 154, respectively. Discharge was performed for one hour, then a pulse depolarization type current (frequency 40 kHz and duty ratio 30%) was passed for three hours at 5.0 V constant voltage. At this time, use was made of a silver chloride electrode (o), carbon electrode (Δ), or aluminum electrode (□) for the negative electrode 155 (2.54 $cm^2$). Note that use was made of silver electrodes for all of the positive electrodes 156 (2.54 $cm^2$). The assay of the dexamethasone sodium phosphate released into the drug receiving container was performed by high pressure liquid chromatography (HPLC) using an opposite phase separation system with a column in which silica gel coupled with octadecyl radicals (ODS), are filled. These results show, like FIGS. 3(A) to (C), that a silver chloride electrode is extremely effective in administration of dexamethasone sodium phosphate compared with a carbon or aluminum electrode. FIGS. 12(A) and (B) show the changes along with time in the average current (1 m) at the time of the experiment and the effective current (Ie), which is comprised of the average current minus the current component flowing in the opposite direction at the time of depolarization. When a constant voltage is charged, there is no great difference in the three types of electrodes in terms of the average current, but when the effective current is compared, a silver chloride electrode exhibits a much higher value compared with the other two types of electrodes. These results show the superiority of a nonpolarized electrode to a polarized electrode in pulse depolarization type iontophoresis.

In this way, if use is made of a reversible (nonpolarized) silver chloride electrode in pulse depolarization type iontophoresis, a higher drug transmission can be achieved at the same power compared with the case of use of another polarized electrode. Further, when the same amount of drug is transmitted, the amount of current and the power used can be slashed. By using the iontophoresis electrode structure of the present invention, it is possible to improve the efficiency of drug transmission in the case of use of a reversible (nonpolarized) electrode such as a silver chloride electrode where chlorine ions etc. are discharged along with conduction and the transport rate of the drug falls. Accordingly, the use of the electrode structure of the present invention leads to an improved feeling of use accompanying the reduction of the irritation to the skin at the time of performance of iontophoresis due to the pulse depolarization method etc. and the reduction of weight of the battery used.

Next, experiments regarding the embodiment of the second aspect of the device of the present invention will be shown in Experiment 2 and Experiment 3. Both cases are examples of using a silver electrode for the positive electrode and a silver chloride electrode for the negative electrode to make dexamethasone sodium phosphate pass through the excised hairless rat skin by iontophoresis in the direction from the negative electrode to the positive electrode. In Experiment 2, no drug holding member was used, but use was made of a drug container containing the drug solution. In Example 3, use was made of a structure based on the embodiment of FIG. 10, that is, a structure having a drug holding member.

EXPERIMENT 2

(Suppression of flow of chlorine ions by positive ion exchange membrane and effect on drug transmission)

FIG. 13 is a sectional view of the experimental apparatus used for the experiment, (a) is a three-container type, wherein provision is made of a conductive solution container 158 in addition to the drug container 151 and drug receiving container 152. The drug container 151 and the conductive drug container 158 are separated by the positive ion exchange membrane (Neosepta (registered trademark) CMS) made by Tokuyama Soda Co.); (b) is a two-container type used for the control experiment and is the same as that used in Experiment 1. The drug container 151 and the drug receiving container 152 are filled with a 5 percent aqueous dexamethanzone sodium phosphate solution 153 and a phosphate buffered saline solution (PBS) 154. The conductive solution container 158 was filled with 30 mM sodium chloride 159. For the cathode 155 and the anode 156, use was made of a silver chloride electrode and a silver electrode, respectively. Discharge was performed for one hour, then conductance was performed at 3.0 mA constant current (frequency 40 kHz and duty ratio of 30%) for three hours. The results, as shown in FIGS. 14(A) and (B), showed that the movement of the chlorine ions to the drug was suppressed by the positive ion exchange membrane (Neosepta (registered trademark) CMS) (a) and that the transmission efficiency of the drug rose (b).

Figure 14B:
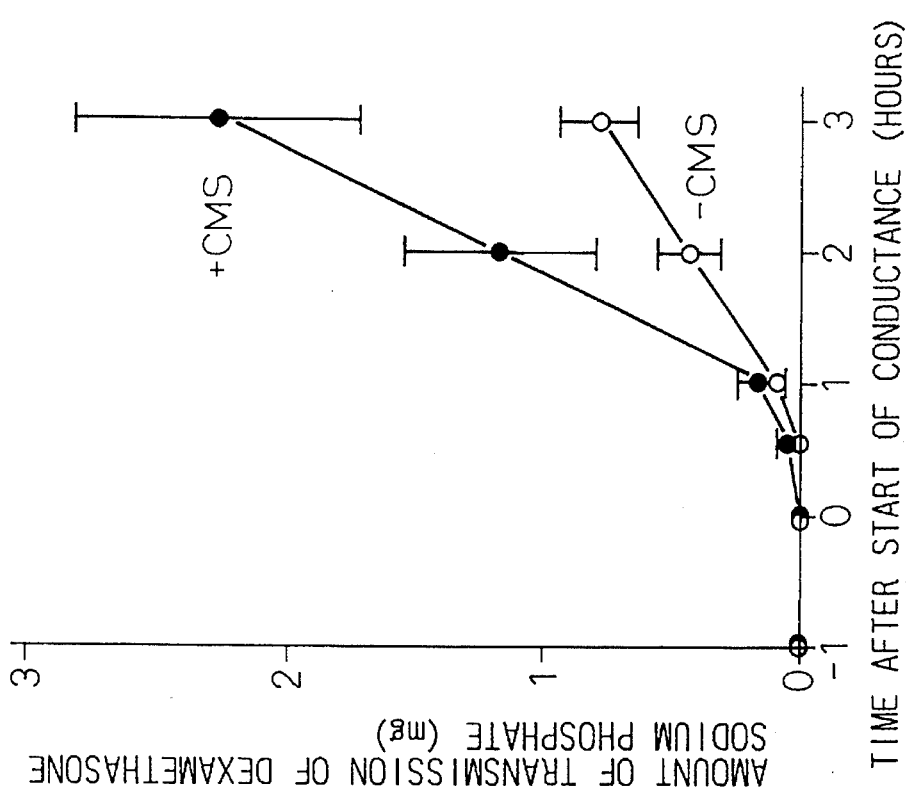
FIGS. 14(A) and (B) are a view showing the results of Experiment 2.
Figure 14A:
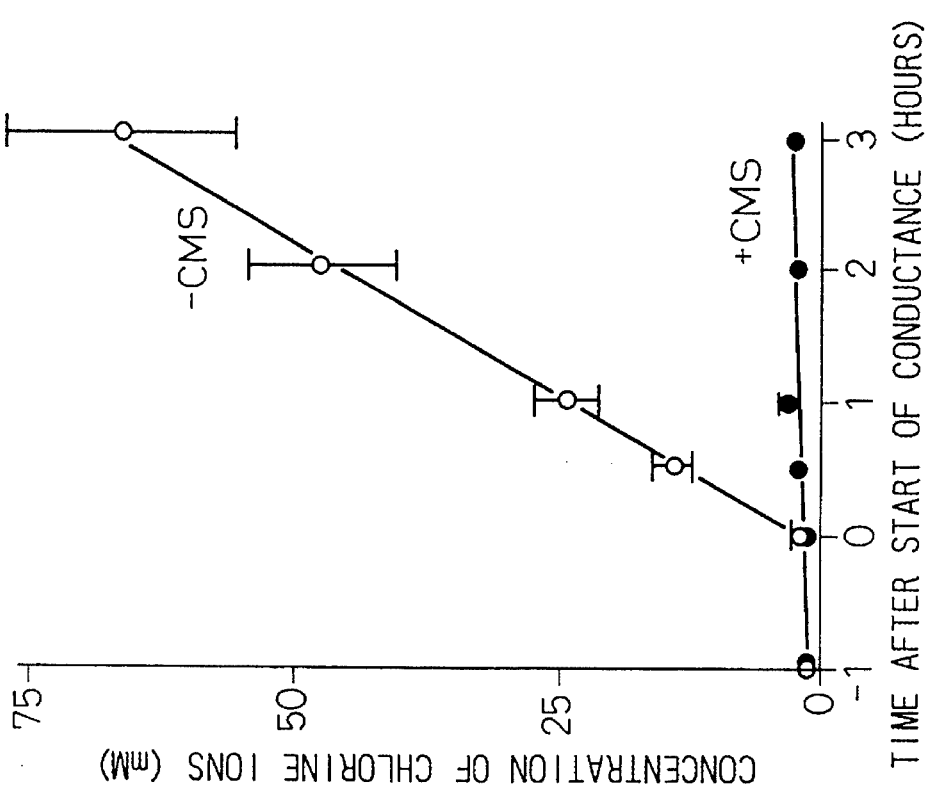
Figure 16:
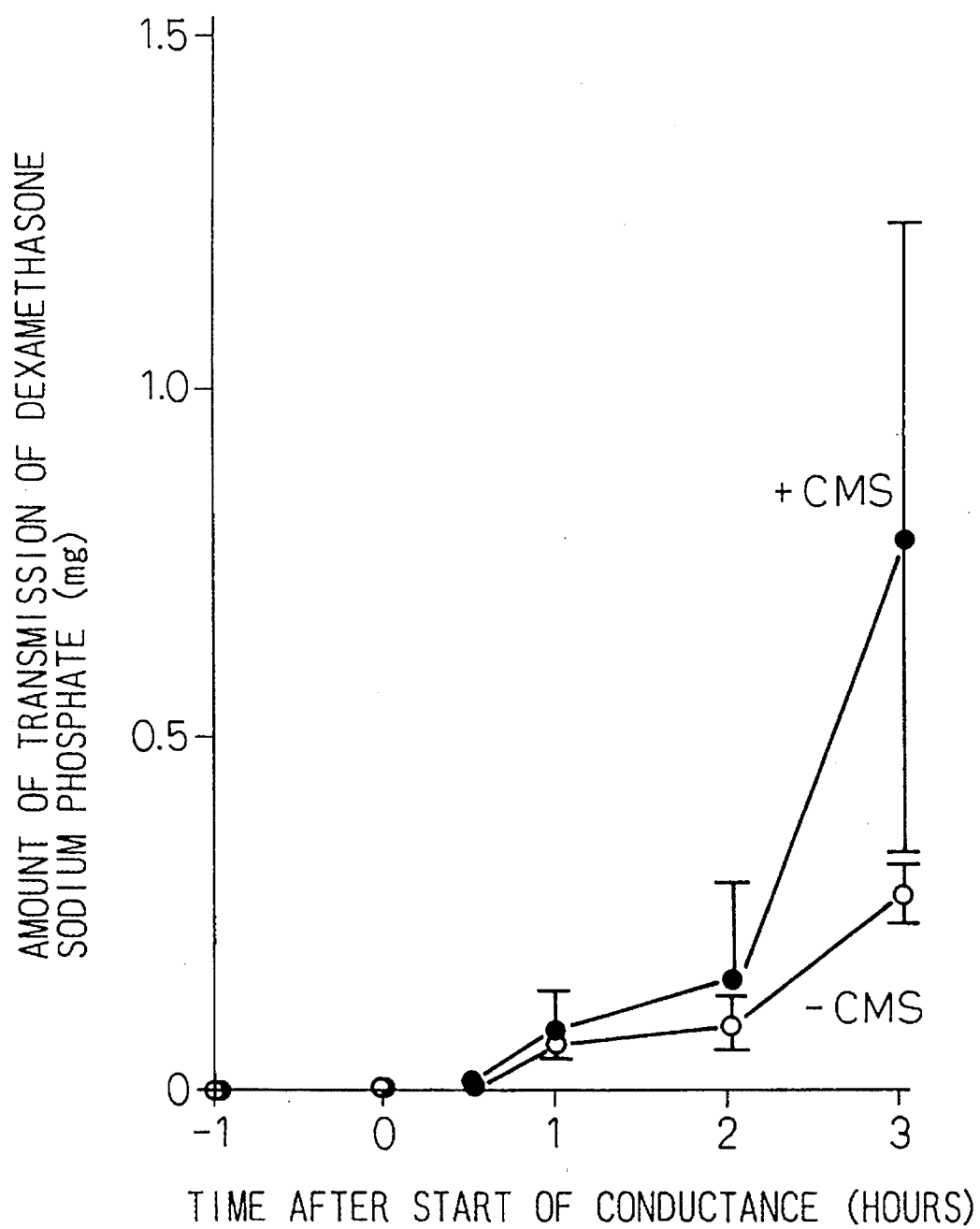
FIG. 16 is a view showing the results of Experiment 3.

Note that, regarding graphs in FIGS. 14(A) and (B) and FIG. 16, the graph with symbol +CMS denotes the embodiment in which the CMS film was used, while the graph with symbol −CMS denotes the embodiment in which the CMS film was not used.

EXPERIMENT 3

(Application of the electrode structure of the present invention to the preparation of the type dissolved at the time of use)

Figure 15A:
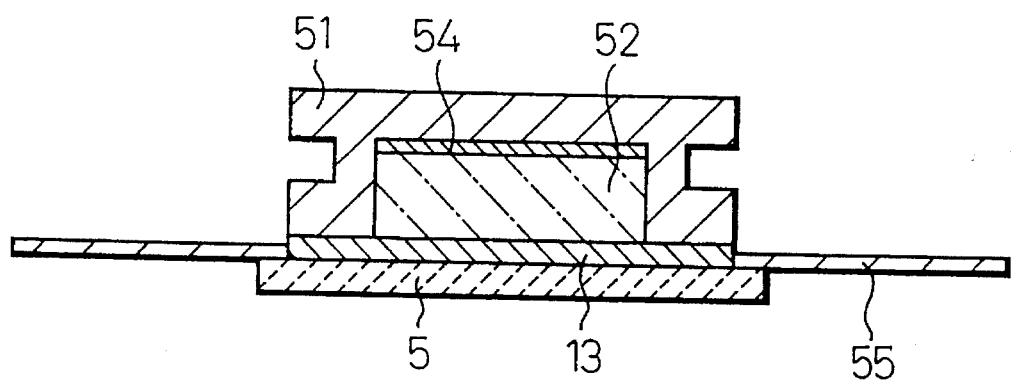
FIGS. 15(A) and (B) are a sectional view of the experimental apparatus in the experiment on the third embodiment of the present invention.
Figure 15B:
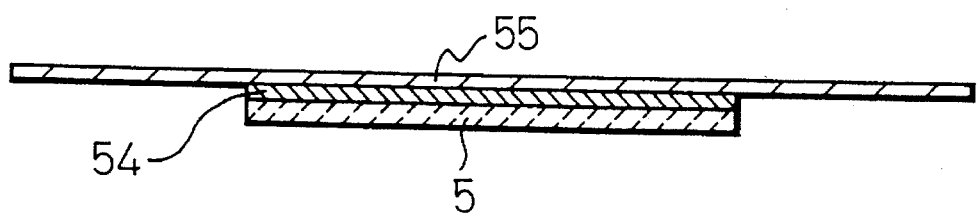

FIG. 15 is a sectional view of the experimental device used for this experiment; (a) includes the electrode structure of the present invention and is based on the embodiment of FIG. 10. The aqueous solution supply member 51 has a silver chloride electrode 54 attached to it. A 30 mM aqueous sodium chloride solution 52 is brought in contact with the drug holding member 5 including 18 mg of dexamethasone sodium phosphate through a positive ion exchange membrane (Neosepta CMS) 13; (b) is a structure for the control experiment, where a silver chloride electrode 54 is brought into direct contact with the drug holding member 5. The drug is stored in a dry state on the drug holding member 5. The aqueous solution is directly added to the drug holding member just before use so as to dissolve the same. For the drug receiving container, use is made of the one shown in FIG. 13. For the positive electrode, use was made of a silver electrode. The result, as shown in FIG. 16, was that the electrode structure of the present invention was effective in improving the drug transmission rate even in the case of a structure having a drug holding member.

As explained in detail above, the electrode structure of the present invention is particularly effective in pulse depolarization type iontophoresis (Japanese Examined Patent Publication (Kokoku) No. 2-45461) proposed previously by the present applicant. That is, in this type, it is possible to obtain the effect of an increase of the effective current (nonpolarized current) through use of the reversible electrode and prevention of the drop of the transport rate by the above-mentioned ion exchange membrane.

We claim:

1. An iontophoresis device comprising:
    a reversible electrode;
    a counter electrode;
    an auxiliary electrode for regeneration of said reversible electrode;
    a drug holding means for carrying an ionic drug therein, said drug holding means being arranged opposite to said reversible electrode and said auxiliary electrode and being constructed to make contact with a surface requiring therapy; and
    a voltage applying control means for applying to said reversible electrode a voltage having a preset voltage level at a preset timing, said voltage applying control means including
    first means for providing depolarized pulses between said reversible electrode and said counter electrode;
    second means for providing a regeneration electrical output between said reversible electrode and said auxiliary electrode when said depolarized pulses are not provided, the polarity of said reversible electrode when said depolarized pulses are not provided being reverse to the polarity of said reversible electrode when said depolarized pulses are provided; and
    switching means for breaking an electrical connection between said auxiliary electrode and said second means when said depolarized pulses are provided.

2. An iontophoresis device according to claim 1, wherein said auxiliary electrode is arranged integrally with said reversible electrode.

3. An iontophoresis device according to claim 1, wherein said voltage applying control means further comprises means for applying to said auxiliary electrode preset pulses at a timing where preset pulses are not applied to said reversible electrode.

4. An iontophoresis device according to claim 1 wherein said voltage applying control means further comprises means for applying to said auxiliary electrode a preset voltage selected from a direct current voltage and a pulse voltage.

5. An iontophoresis device according to claim 1, wherein said voltage applying control means further comprises means for applying to said counter electrode preset pulses having a different phase than preset pulses applied to said reversible electrode.

6. An iontophoresis device according to claim 1, wherein said auxiliary electrode is provided at a position close to said reversible electrode.

7. An iontophoresis device according to claim 1, wherein said auxiliary electrode is provided on a plane of said device identical to the plane on which said reversible electrode is provided.

8. An iontophoresis device according to claim 1, wherein said auxiliary electrode is provided to form a construction in which said auxiliary electrode is stacked with said reversible electrode through a supporting means interposed therebetween.

9. An iontophoresis device according to claim 8; wherein said auxiliary electrode and said reversible electrode 18 made of a material having a function enabling water to penetrate therethrough.

10. An iontophoresis device according to claim 8, wherein said supporting means is made of a material having a function enabling water to penetrate therethrough.

11. An iontophoresis device according to claim 1, and further comprising
    an ion exchange film having an opposite polarity of said reversible electrode, said ion exchange film being disposed between said reversible electrode and said drug holding means.

12. An ionthophoresis device according to claim 11, wherein a conductive solution is interposed between said ion exchange film and said reversible electrode.

13. An iontophoresis device according to claim 11 or 12 further comprising a drug solution supply means connected to said drug holding means.

* * * * *

UNITED STATES PATENT AND TRADEMARK OFFICE
CERTIFICATE OF CORRECTION

PATENT NO. : 5,620,580
DATED : April 15, 1997
INVENTOR(S) : Keiichiro Okabe; Toyoji Hibi It is certified that error appears in the above-indentified patent and that said Letters Patent is hereby corrected as shown below:

Abstract, line 3, change "covering" to -- covered --.
Abstract, line 5, change " Provision" to --, provision --.
Column 1, line 20, change "covering" to --covered --.
Column 1, line 58, change "an. auxiliary " to -- an auxiliary --.
Column 2, line 38, after "comprises" change the semi-colon to a colon.
Column 2, line 42, after "being" delete the colon.
Column 2, line 65, change "electrode 3," to -- electrode 3. --.
Column 3, line 39, change "means .which" to -- means which --.
Column 4, line 26, delete "abut".
Column 4, line 37, change "electrode i" to -- electrode 1--.
Column 4, line 58, after "electrode" delete -- and --.
Column 4, line 59, before "applies" insert -- and --.
Column 5, line 56, after "is" and before "drug" insert -- a --.
Column 5, line 61, change "bolding" to -- holding --.
Column 5, line 67, change "electrode-and" to -- electrode and --.
Column 6, line 29, change "ionophoresis" to - - iontophoresis --.
Column 6, line 55, change "Terrenadine" to -- Terfenadine--.
Column 8, line 13, change "titrate" to -- citrate--.
Column 8, line 38, change "abirriant" to -- abirritant--.
Column 9, line 13, change "Carvedilo1" to -- Carvedilol--.
Column 10, line 10, change "electrode," to -- electrode.--.
Column 10, line 47, change "40 kMz" to -- 40 kHz--.
Column 10, line 57, after "was" and before "15" insert -- approximately --.
Column 10, line 61, before "output" change "were" to --was--.

UNITED STATES PATENT AND TRADEMARK OFFICE
CERTIFICATE OF CORRECTION

PATENT NO. : 5,620,580
DATED : April 15, 1997
INVENTOR(S) : Keiichiro Okabe; Toyoji Hibi It is certified that error appears in the above-indentified patent and that said Letters Patent is hereby corrected as shown below:

Column 11, line 16, change "resul" to -- result --.
Column 11, line 57, change "effects" to -- effect --.
Column 11, line 61, change "drug-" to -- drug --.
Column 12, line 32, change "or," to -- of --.
Column 12, line 57, change "(registered. trademark)" to
  -- (registered trademark) --
Column 13, line 50, change "minus-the" to -- minus the --.
Column 13, line 63, change "compared. with" to -- compared with --
.Column 13, line 66, change "slashed," to -- slashed. --.
Column 14, line 39, change "dexamethanzone" to-- dexamethazone --
.Column 15, line 9, change "member Just" to -- member just --.
Column 16, line 32, change "claim 8;" to -- claim 8, --.
Column 16, line 33, change "electrode 18" to -- electrode is --.

Signed and Sealed this

Thirtieth Day of June, 1998

*Attest:*

BRUCE LEHMAN

*Attesting Officer*           *Commissioner of Patents and Trademarks*